(12) United States Patent
Mishima et al.

(10) Patent No.: US 8,377,026 B2
(45) Date of Patent: Feb. 19, 2013

(54) ABSORBENT WEARING ARTICLE AND METHOD FOR MAKING THE SAME

(75) Inventors: Yoshitaka Mishima, Kagawa (JP); Kyo Kikuchi, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 245 days.

(21) Appl. No.: 12/681,917

(22) PCT Filed: Aug. 13, 2008

(86) PCT No.: PCT/JP2008/064535
§ 371 (c)(1),
(2), (4) Date: Aug. 19, 2010

(87) PCT Pub. No.: WO2009/047944
PCT Pub. Date: Apr. 16, 2009

(65) Prior Publication Data
US 2010/0312213 A1    Dec. 9, 2010

(30) Foreign Application Priority Data

Oct. 9, 2007  (JP) ................................ 2007-263693

(51) Int. Cl.
*A61F 13/475* (2006.01)
*B32B 37/00* (2006.01)
(52) U.S. Cl. ............... 604/385.28; 604/385.01; 156/202
(58) Field of Classification Search . 604/385.27–385.28
See application file for complete search history.

(56) References Cited

U.S. PATENT DOCUMENTS

| | | | | |
|---|---|---|---|---|
| 4,816,025 A | * | 3/1989 | Foreman | 604/385.27 |
| 4,892,536 A | * | 1/1990 | DesMarais et al. | 604/385.27 |
| 4,990,147 A | * | 2/1991 | Freeland | 604/385.22 |
| 5,061,261 A | * | 10/1991 | Suzuki et al. | 604/385.25 |
| 5,167,653 A | * | 12/1992 | Igaue et al. | 604/385.04 |
| 5,246,432 A | * | 9/1993 | Suzuki et al. | 604/385.25 |
| 5,292,316 A | * | 3/1994 | Suzuki | 604/385.26 |

(Continued)

FOREIGN PATENT DOCUMENTS

JP   2003-038559   2/2003

OTHER PUBLICATIONS

International Search Report from corresponding PCT application No. PCT/JP2008/064535, dated Nov. 18, 2008, 2 pages.

*Primary Examiner* — Melanie Hand
*Assistant Examiner* — Paula Craig
(74) *Attorney, Agent, or Firm* — Brinks Hofer Gilson & Lione

(57) ABSTRACT

The present invention aims to provide an absorbent wearing article being capable of alleviating irritation to the wearer's skin as well as to be easily produced and a method for making the same.

A liquid-absorbent chassis 4 is provided with a barrier cuff 5 including first and second barrier cuffs 5a, 5b each comprising an outermost edge 21, an innermost edge 24 and front and rear ends 22, 23 opposed to and spaced from each other in a longitudinal direction Y. The outermost edge 21 as well as the front and rear ends 22, 23 are joined to a topsheet 10 to define a fixed edge and the innermost edge 24 is not joined to the topsheet 10 to define a free edge adapted to be freely spaced from the liquid-absorbent chassis 4. Of the first and second barrier cuffs 5a, 5b, at least the fixed edge is formed by an inelastic, substantially non-extensible first sheet 25 while the free edge is formed by an elastically extensible second sheet 26. The first sheet 25 is formed along its innermost edge 24 with a notch 27 in which the second sheet 26 is exposed.

6 Claims, 5 Drawing Sheets

U.S. PATENT DOCUMENTS

| | | | | |
|---|---|---|---|---|
| 5,342,342 | A * | 8/1994 | Kitaoka | 604/385.19 |
| 5,344,516 | A * | 9/1994 | Tanji et al. | 156/164 |
| 5,417,680 | A * | 5/1995 | Kimura et al. | 604/385.28 |
| 5,439,459 | A * | 8/1995 | Tanji et al. | 604/385.28 |
| 5,476,458 | A * | 12/1995 | Glaug et al. | 604/378 |
| 5,536,563 | A * | 7/1996 | Shah et al. | 442/329 |
| 5,593,401 | A * | 1/1997 | Sosalla et al. | 604/385.28 |
| 5,649,918 | A * | 7/1997 | Schleinz | 604/385.26 |
| 5,674,213 | A * | 10/1997 | Sauer | 604/385.01 |
| 5,830,203 | A * | 11/1998 | Suzuki et al. | 604/385.19 |
| 5,873,868 | A * | 2/1999 | Nakahata | 604/383 |
| 5,931,826 | A * | 8/1999 | Faulks et al. | 604/385.27 |
| 5,957,907 | A * | 9/1999 | Sauer | 604/385.24 |
| 5,993,433 | A * | 11/1999 | St. Louis et al. | 604/385.27 |
| 6,022,338 | A * | 2/2000 | Putzer | 604/385.01 |
| 6,102,892 | A * | 8/2000 | Putzer et al. | 604/385.01 |
| 6,120,486 | A * | 9/2000 | Toyoda et al. | 604/385.29 |
| 6,132,409 | A * | 10/2000 | Vogt et al. | 604/348 |
| 6,217,563 | B1 * | 4/2001 | Van Gompel et al. | 604/385.101 |
| 6,248,098 | B1 * | 6/2001 | Sayama | 604/385.28 |
| 6,323,389 | B1 * | 11/2001 | Thomas et al. | 604/370 |
| 6,328,724 | B1 * | 12/2001 | Ronnberg et al. | 604/385.24 |
| 6,383,170 | B1 * | 5/2002 | Mishima et al. | 604/385.19 |
| 6,402,729 | B1 * | 6/2002 | Boberg et al. | 604/385.28 |
| 6,423,048 | B1 * | 7/2002 | Suzuki et al. | 604/385.28 |
| 6,527,756 | B1 * | 3/2003 | Mishima et al. | 604/385.19 |
| 6,592,562 | B2 * | 7/2003 | Menard et al. | 604/385.04 |
| 6,629,967 | B1 * | 10/2003 | Simmons et al. | 604/385.27 |
| 6,659,993 | B2 * | 12/2003 | Minato et al. | 604/385.27 |
| 6,716,205 | B2 * | 4/2004 | Popp et al. | 604/385.24 |
| 6,786,895 | B1 * | 9/2004 | Schmitz | 604/385.28 |
| 6,913,599 | B2 * | 7/2005 | Mishima et al. | 604/385.08 |
| 7,008,408 | B2 * | 3/2006 | Otsubo | 604/385.01 |
| 7,648,490 | B2 * | 1/2010 | Kuroda et al. | 604/385.01 |
| 7,654,993 | B2 * | 2/2010 | Arizti et al. | 604/385.27 |
| 7,942,859 | B2 * | 5/2011 | Nakajima et al. | 604/385.27 |
| 8,007,614 | B2 * | 8/2011 | Schneider et al. | 156/163 |
| 8,062,279 | B2 * | 11/2011 | Miyamoto | 604/385.27 |
| 2001/0021838 | A1 * | 9/2001 | Mizutani et al. | 604/385.28 |
| 2001/0023343 | A1 * | 9/2001 | Mizutani et al. | 604/385.28 |
| 2001/0039408 | A1 * | 11/2001 | Tanji et al. | 604/385.26 |
| 2002/0029028 | A1 * | 3/2002 | Shimada et al. | 604/385.28 |
| 2002/0029029 | A1 * | 3/2002 | Otsubo | 604/385.101 |
| 2002/0040215 | A1 * | 4/2002 | Suzuki | 604/385.28 |
| 2003/0023225 | A1 * | 1/2003 | Sayama | 604/385.28 |
| 2004/0005835 | A1 * | 1/2004 | Zhou et al. | 442/328 |
| 2004/0092900 | A1 * | 5/2004 | Hoffman et al. | 604/380 |
| 2004/0153044 | A1 * | 8/2004 | Kuen et al. | 604/385.28 |
| 2005/0273072 | A1 * | 12/2005 | Hird et al. | 604/385.24 |
| 2006/0025744 | A1 * | 2/2006 | Mishima et al. | 604/385.101 |
| 2006/0058765 | A1 * | 3/2006 | Mueller et al. | 604/385.19 |
| 2007/0191807 | A1 * | 8/2007 | Hayashi et al. | 604/385.28 |
| 2007/0244455 | A1 * | 10/2007 | Hansson et al. | 604/385.201 |

\* cited by examiner

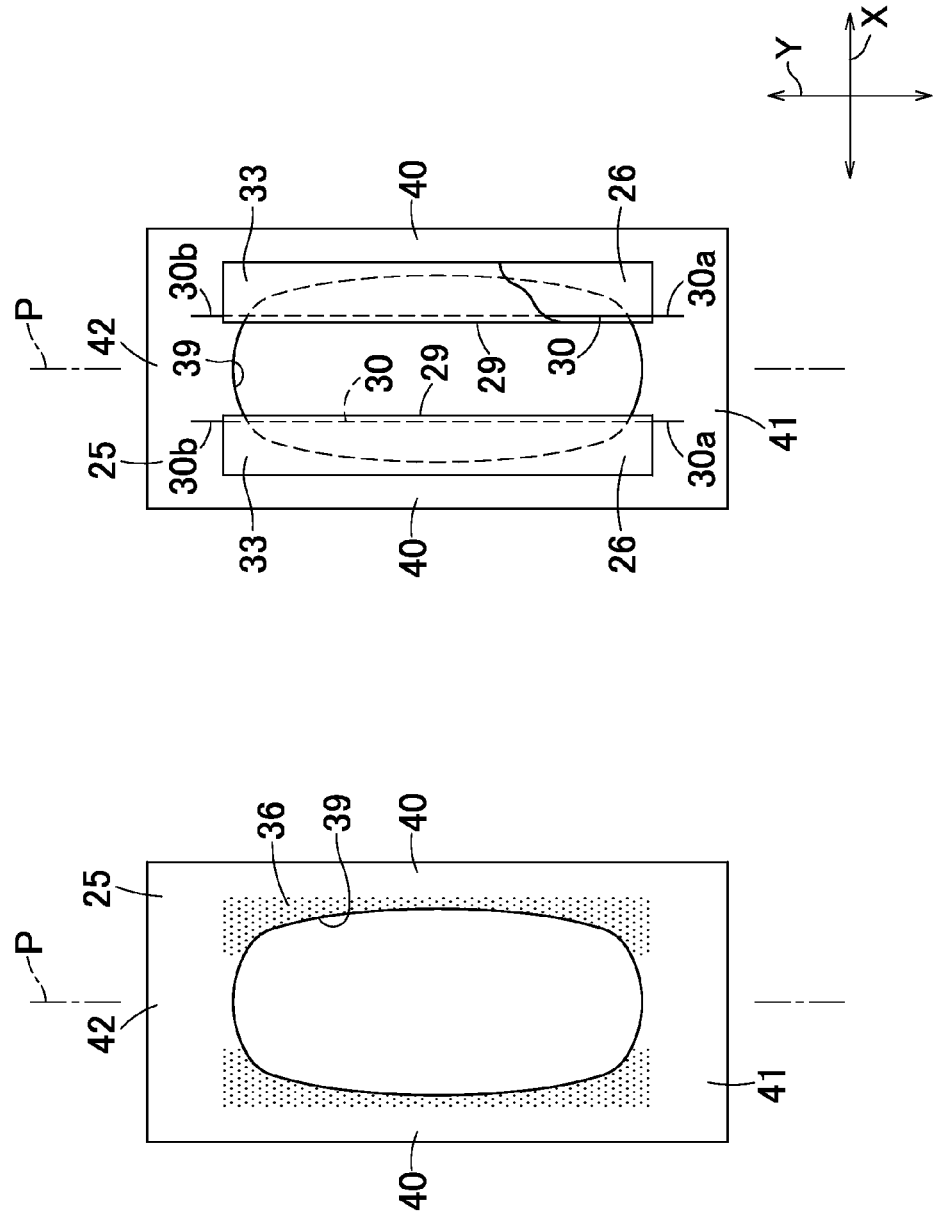

ABSORBENT WEARING ARTICLE AND METHOD FOR MAKING THE SAME

RELATED APPLICATION

This application is a 35 U.S.C. §371 national phase filing of International Patent Application No. PCT/JP2008/064535, filed Aug. 13, 2008, through which and to which priority is claimed under 35 U.S.C. §119 to Japanese Patent Application No. 2007-263693, filed Oct. 9, 2007.

TECHNICAL FIELD

The present invention relates to an absorbent wearing article and more particularly to an absorbent wearing article such as a disposable diaper, toilet-training pants or incontinent briefs and a method for making the same.

RELATED ART

Diapers provided with barrier cuffs is known, for example, from the disclosure of JP2003-38599A. The diaper disclosed in JP2003-38599A comprises a liquid-absorbent chassis and a barrier cuffs of a pair of barrier cuffs opposed to and spaced from each other symmetrically about a longitudinal center line. Each of the cuffs is formed from an elasticized fibrous nonwoven fabric and has a fixed side edge lying along the associated side edge of the diaper, a free edge lying aside toward the longitudinal center line of the diaper and an elastic member extending in a longitudinal direction of the diaper along the associated free edge. With the diaper put on the wearer's body, the liquid-absorbent chassis is curved and the free edges are spaced from the liquid-absorbent chassis toward the wearer's skin as the barrier cuffs contract under the effect of the elastic members. The barrier cuffs raise itself as the free edges are spaced from the liquid-absorbent chassis, allowing it possible to prevent body waste from leaking out.
PATENT DOCUMENT 1: JP2003-38599A

DISCLOSURE OF THE INVENTION

Problem to be Solved by the Invention

In the diaper disclosed in JP2000-288915A, the barrier cuffs as a whole is formed from of an elastically extensible fibrous nonwoven fabric or inelastic, substantially non-extensible fibrous nonwoven fabric. When the barrier cuffs are formed from the inelastic fibrous nonwoven fabric, the free edges form gathers under contraction of the elastic members attached to the respective free edges and these gathers irritate the wearer's skin. From a viewpoint of skin irritation to be alleviated, use of such material is problematic. When the barrier cuffs are formed from the elasticized fibrous nonwoven fabric, formation of gathers is certainly restrained. However, it is difficult to handle such elasticized fibrous nonwoven fabric and, in consequence, use of such elasticized fibrous nonwoven fabric is problematic to make the barrier cuffs. Specifically, the usual method for making the disposable diaper includes the step of cutting the fibrous nonwoven fabric drawn forth from a feed roll under a given tension in a desired shape. In this step, the elasticized fibrous nonwoven fabric is inevitably extended as being drawn forth and therefore the fibrous nonwoven fabric is in an extended state when it is cut in the desired shape. Upon contraction of such cut off piece, the piece no more has the desired shape and to overcome this problem, any special equipment other than the equipment conventionally used in this field must be used. Consequentially, use of the elasticized fibrous nonwoven fabric makes the production difficult or complicated.

In view of the problem as has been described above, it is an object of the present invention to provide an absorbent wearing article being capable of alleviating irritation to the wearer's skin as well as to be easily produced and a method for making the same.

Measure to Solve the Problem

According to the present invention, there is provided absorbent wearing article comprising a liquid-absorbent chassis having a longitudinal direction, a transverse direction, an inner side facing the article wearer's skin, an outer side facing the article wearer's garment, a front waist region, a rear waist region, a crotch region between these front and rear waist regions and a liquid-absorbent structure provided so as to occupy at least the crotch region, and a barrier cuff provided on the inner side facing the wearer's skin of the liquid-absorbent chassis so as to extend in the longitudinal direction.

According to the present invention is characterized in that the barrier cuff comprises a pair of first and second barrier cuffs opposed to and spaced from each other symmetrically about a longitudinal center line bisecting a dimension of the article in the transverse direction so as to extend in the longitudinal direction, each of the first and second barrier cuffs comprising an outermost edge extending in the longitudinal direction, an innermost edge lying aside from the outermost edge toward the longitudinal center line, a fixed edge formed by an inelastic first sheet fixed to the liquid-absorbent chassis at least in the vicinity of the outermost edge and a free edge being spaceable from the liquid-absorbent chassis at least partially along the innermost edge and formed by an elastically extensible second sheet, and the second sheet being attached to the first sheet under tension in the longitudinal direction so that, with the absorbent wearing article put on the wearer's body, possible formation of gathers along the innermost edges in the longitudinal direction may be deactivated.

Expression "elastically extensible second sheet" used herein refers to the sheet itself being elasticized and depending on no other component such as elastic member. Expression "possible formation of gathers is deactivated" used herein means that formation of gathers is restricted or substantially none of gathers appears.

According to one preferred embodiment, with the absorbent wearing article flatly developed, a sum of respective dimensions of the pair of first and second barrier cuffs as measured in the transverse direction is in a range of 40% to 95% of a dimension of the absorbent wearing article in the crotch region as measured in the transverse direction.

According to another preferred embodiment, the barrier cuff includes front and rear ends opposed to and spaced from each other in the longitudinal direction and cuff biasing elastic members attached under tension to the barrier cuff so as to extend in the longitudinal direction from the front end to the rear end, the front and rear ends being formed by the first sheet, and front and rear ends of the cuff biasing elastic members being fixed to the front and rear ends formed by the first sheet.

According to still another preferred embodiment, the barrier cuff has the outermost edges as well as the front and rear ends formed by the first sheet, the innermost edges formed with notches and the second sheet joined to the first sheet so as to fill the notches.

According to yet another preferred embodiment, the second sheet is partially sandwiched and affixed between two layers of the first sheet having been folded back.

According to further another preferred embodiment, a stiffness of the first sheet is set to be higher than a stiffness of the second sheet.

The present invention relates to an improvement in the absorbent wearing article comprising a liquid-absorbent chassis having a longitudinal direction, a transverse direction, an inner side facing the wearer's skin, an outer side facing the article wearer's garment, a front waist region, a rear waist region, a crotch region between these front and rear waist regions and a liquid-absorbent structure provided so as to occupy at least said crotch region, and a barrier cuff provided on the inner side facing the wearer's skin of the liquid-absorbent chassis so as to extend in the longitudinal direction. The present invention relates also to a method for making such improved absorbent wearing article and comprises the steps of making the liquid-absorbent chassis, making the barrier cuff, attaching the barrier cuff to the liquid-absorbent chassis wherein the step of making the barrier cuff comprises the steps of forming an inelastic first sheet with a pair of openings spaced from each other in the transverse direction symmetrically about a longitudinal center line bisecting a dimension of the first sheet and extending in the longitudinal direction, joining an elastically extendible second sheet under tension to the first sheet so as to cover the openings, attaching elastic members under tension to the first sheet at front and rear ends to the elastic members along a fold line bisecting a dimension of the openings as measured in the transverse direction, and cutting the first sheet to which the second sheet has been joined along the longitudinal center line and then folding back the first and second sheets along the fold line.

Effect of the Invention

According to the present invention, the free edges of the barrier cuff are at least partially formed by the elastically extensible second sheet and the fixed edges are formed by the inelastic, substantially non-extensible first sheet so that use of the second sheet which is difficult to handle may be minimized. The shape of the barrier cuff as a whole can be defined by the first sheet so that production of the barrier cuff, eventually of the absorbent wearing article as a whole can be facilitated.

By forming the free edges of the barrier cuff by the second sheet, it is possible to avoid a possibility that contraction of the barrier cuff might result in formation of gathers and thereby to alleviate irritation of the wearer's skin.

BRIEF DESCRIPTION OF THE DRAWINGS

FIGS. 7A and 7B are schematic diagrams illustrating the method for making the barrier cuffs according to the second embodiment.

Figure 1:
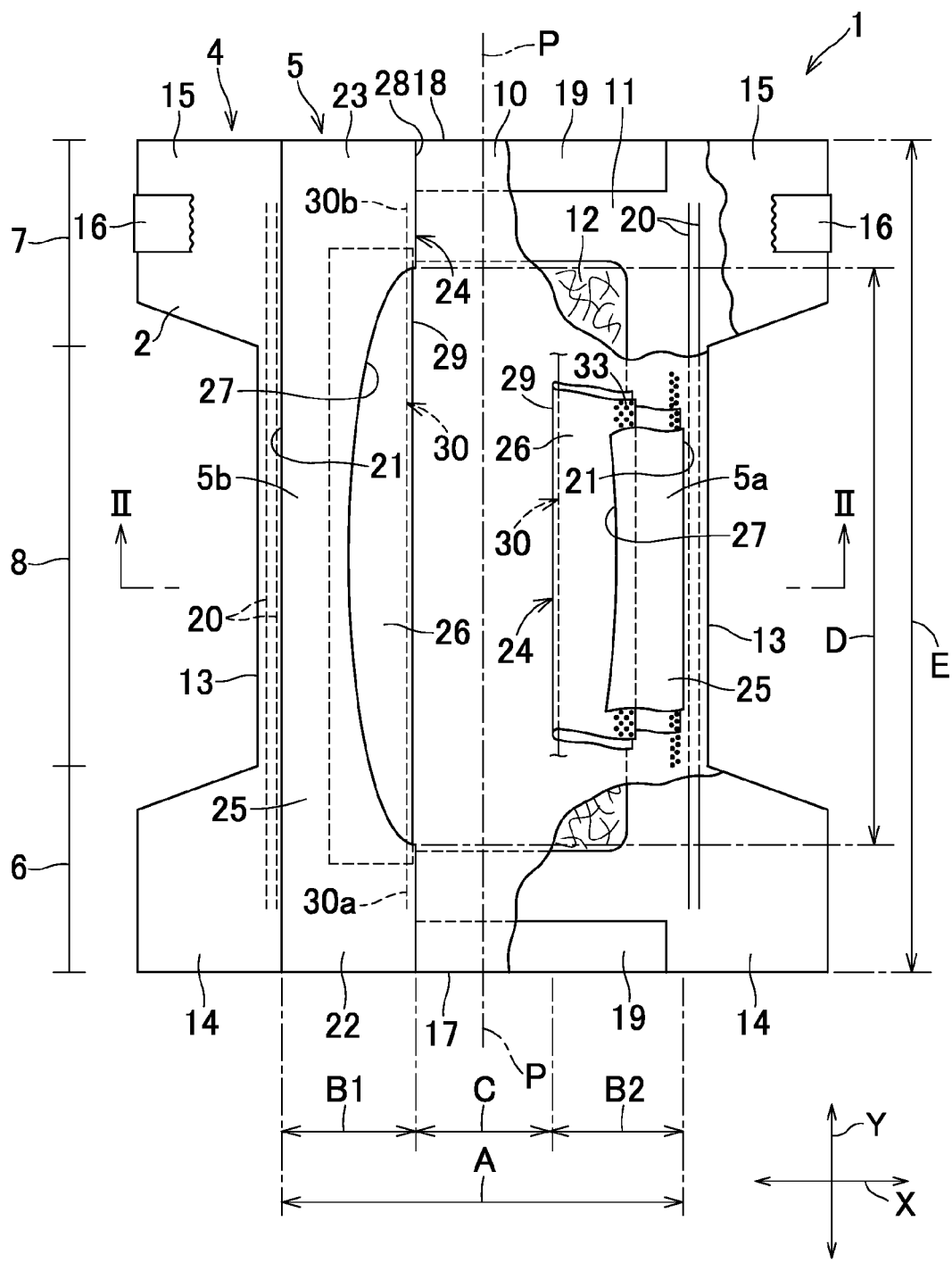
FIG. 1 is a plan view showing a diaper according to a first embodiment of the present invention.

IDENTIFICATION OF REFERENCE NUMERALS USED IN THE DRAWINGS 2 inner side facing wearer's skin
3 outer side facing wearer's clothes
4 liquid-absorbent chassis
5 barrier cuff
5a first barrier cuff
5b second barrier cuff
6 front waist region
7 rear waist region
8 crotch region
21 outermost edge
22 front end
23 rear end
24 innermost edge
25 first sheet
26 second sheet
27 notch
28 fold line
29 fold line
30 cuff biasing elastic member
30a front end
30b rear end

DESCRIPTION OF THE BEST MODE FOR WORKING OF THE INVENTION

First Embodiment

FIGS. 1 through 5 illustrate a first embodiment of the present invention.

FIG. 1 is a plan view showing a diaper 1 on the assumption that a contractile force of respective elastic members and elasticized sheet is inactivated. The diaper 1 as an example of the absorbent wearing article comprises a liquid-absorbent chassis 4 having an inner side 2 facing the wearer's skin and an outer side 3 facing the wearer's garment and barrier cuffs 5 provided on the inner side 2 of the liquid-absorbent chassis 4 so as to extend in a longitudinal direction Y. FIG. 1 assumes that a front side of the draft sheet corresponds to the inner side 2 facing the wearer's skin and a backside of the draft sheet corresponds to the outer side 3 facing the wearer's garment.

The liquid-absorbent chassis 4 has a front waist region 6, a rear waist region 7 and a crotch region 8 between these front and rear waist regions 6, 7 and comprises a cover sheet and a liquid-absorbent structure attached to the cover sheet at least in the crotch region 8. The cover sheet comprises a liquid-pervious topsheet 10 lying on the inner side 2 facing the wearer's skin and a liquid-impervious backsheet 11 lying on the outer side 3 facing the wearer's garment wherein a liquid-absorbent core 12 wrapped with tissue paper or the like is sandwiched between these top- and backsheets 10, 11 as the liquid-absorbent structure.

The liquid-absorbent chassis 4 has a substantially hourglass-like planar shape. More specifically, a pair of side edges 13 opposed to and spaced from each other in the transverse direction so as to extend in the longitudinal direction Y curve in the crotch region 8 concavely toward a longitudinal center line P-P bisecting a width of the crotch region 8. In the front and rear waist regions 6, 7 of the liquid-absorbent chassis 4, portions of the top- and backsheets 10, 11 extending outward from the liquid-absorbent core 12 in the transverse direction X are put flat and bonded or welded to each other to form a front wing 14 and a rear wing 15. The rear wing 15 is coated along opposite side edges 13 with pressure-sensitive adhesive (not shown) by which fastening tapes 16 are attached to the side edges 13 so that these fastening tapes 16 extend outward in the transverse direction X. By means of these fastening tapes 16, the opposite side edges of the front waist region are joined to the corresponding opposite side edges of the rear waist region 7 when the diaper 1 is put on the wearer's body.

The liquid-absorbent chassis 4 includes front and rear ends 17, 18 opposed to and spaced from each other in the longitudinal direction Y and waist elastic members 19 extend along these front and rear ends 17, 18, respectively, in the transverse direction X. The waist elastic members 19 are attached under tension to at least one of the top- and backsheets 10, 11 along portions of these top- and backsheets 10, 11 extending outward from the liquid-absorbent core 12 in the longitudinal direction Y.

The chassis 4 is provided along the opposite side edges 13 with leg elastic members 20. These leg elastic members 20 extend at least fully in the crotch region 8 and preferably further extend into the front and rear waist regions 6, 7. The leg elastic members 20 are attached under tension to at least one of the top- and backsheets 10, 11 along portions of these top- and backsheets 10, 11 extending outward from the liquid-absorbent core 12 in the transverse direction X.

The liquid-absorbent chassis 4 is provided on the inner side facing the wearer's skin with a barrier cuff 5 comprising a pair of first and second barrier cuffs 5a, 5b opposed to and spaced from each other in the transverse direction X. These first and second barrier cuffs 5a, 5b extend from a front end 17 to a rear end 18 of the liquid-absorbent chassis 4 and are configured symmetrically about the longitudinal center line P-P. The first and second barrier cuffs 5a, 5b extend along the leg elastic members 20 slightly inside the respective leg elastic members 20 as viewed in the transverse direction X. The first and second barrier cuffs 5a, 5b respectively include outermost edges 21 as viewed in the transverse direction and extending in the longitudinal direction Y, innermost edges 24 opposed to and spaced from the outermost edges 21 and lying aside from the associated outermost edges 21 toward the longitudinal center line P-P, and front and rear ends 22, 23 opposed to and spaced from each other in the longitudinal direction Y.

The outermost edges 21 and the front and rear ends 22, 23 are joined to the topsheet 10 by bonding or welding to define fixed edges and ends. The innermost edges 24 are not joined to the topsheet 10 and define free edges adapted to be spaced from the liquid-absorbent chassis 4.

Of the first and second barrier cuffs 5a, 5b, at least the fixed edges are formed by an inelastic, substantially non-extensible first sheet 25 while the free edges are formed by an elastically extensible second sheet 26. More specifically, the first sheet 25 is folded back onto itself along a fold line 28 defined by the innermost edges 24. The first sheet 25 is partially cutaway along each of the innermost edges 24 to define a notch 27 curving concavely toward the longitudinal center line P-P.

A second sheet 26 underlies the first sheet 25 and is partially exposed outward beyond the notch 27 to define each of the free edges. The second sheet 26 is folded back onto itself along a fold line 29 defined by each of the innermost edges 24. The second sheet 26 is sandwiched between two layers of the folded first sheet 25 and is joined under tension to the first sheet 25 at a joint zone 33.

The fold line 28 and the fold line 29 are substantially fall on a straight line and these fold lines 28, 29 define each of the innermost edges 24.

The respective innermost edges 24 of the first and second barrier cuffs 5a, 5b are provided along the fold lines 28, 29 with cuff biasing thread-like elastic members 30 attached thereto under tension in the longitudinal direction Y. Front and rear ends 30a, 30b of the respective cuff biasing elastic members 30 are fixed to the inner surface of the first sheet 25 by adhesive bonding or welding technique. In this way, the cuff biasing elastic members 30 are not adhered to second sheet 26, so that elastic members 30 are left free to move longitudinally within fold line 29. Consequentially, there is no possibility that the second sheet 26 might be formed with gathers under the contraction of the cuff biasing elastic members 30 and it is ensured that the second sheet 26 is reliably held in close contact with the wearer's inguinal region so as to restrict formation of a gap between the second sheet 26 and the wearer's skin.

Figure 2:
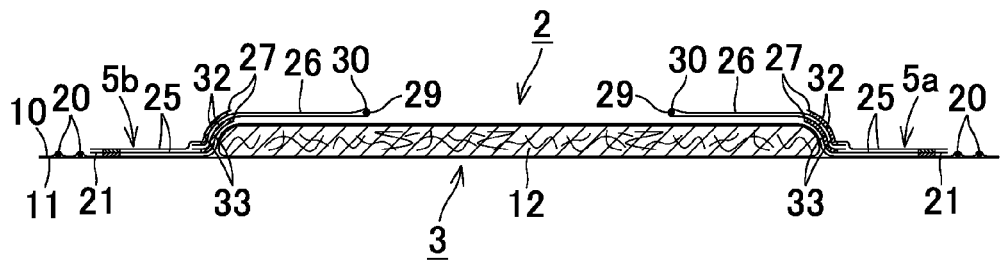
FIG. 2 is the sectional view taken along the line II-II in FIG. 1.

FIG. 2 is a sectional view taken along the line II-II in FIG. 1. As shown, the second sheet 26 is sandwiched between two layers of the folded first sheet 25 wherein the notch 27 of the first sheet 25 and an outside portion 32 of the second sheet 26 are overlapped and joined to each other at the joint zone 33. The cuff biasing elastic member 30 is provided along the fold line 28 and an edge of the second sheet 26 is formed along the fold line 28 as the cuff biasing elastic member 30 contracts. In the first and second barrier cuffs 5a, 5b, the outermost edges 21 each defined by the first sheet 25 are joined to the topsheet 10 to form the respective fixed edges. It should be noted here that each of the fixed edges may be formed by at least a portion of the first sheet 25 and the remaining portion may be spaced from the topsheet 10 so as to form a free edge.

Figure 3:
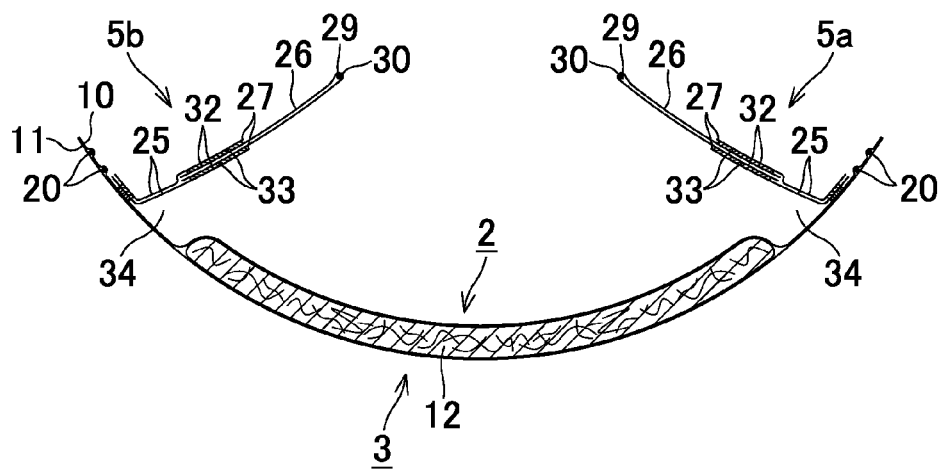
FIG. 3 is a view similar to FIG. 2, showing the diaper as put on the wearer's body.

FIG. 3 is a view similar to FIG. 2, showing the diaper as put on the wearer's body. With the diaper 1 put on the wearer's body, the diaper 1 is curved concavely toward the outside thereof in the crotch region 8 so that the topsheet 10 lies inside and the crotch region 8 also is curved in the transverse direction X as the wearer's legs squeeze the crotch region 8 in the transverse direction X. The elastically extensible second sheet 26 contracts as the diaper 1 is curved and, as shown in FIG. 3, the second sheet 26 constituting the first and second barrier cuffs 5a, 5b is spaced from the topsheet 10. Pockets 34 are formed between the second sheet 26 and the topsheet 10 spaced from each other. At the same time, the cuff biasing elastic members 30 also contract and, in consequence, the edges are formed along the fold lines 29 of the second sheet 26.

The second sheet 26 spaced from the topsheet 10 comes in close contact with the wearer's inguinal region, allowing body waste to be reliably guided into the pockets 34. The second sheet 26 is made of an elastically extensible fibrous nonwoven fabric and therefore none of gathers is formed on its surface even when the second sheet 26 contracts. In consequence, irritation of the wearer's skin due to the second sheet 26 can be drastically alleviated. While some gathers may appear in the second sheet 26 at the joint zone 33 since the second sheet 26 is joined to the inelastic first sheet 25 at this joint zone 33, the second sheet 26 is kept sufficiently spaced from the wearer's skin at this joint zone 33 to protect the wearer's skin from irritation.

With respect to the cuff biasing elastic members 30 attached to the innermost edges 24, a tensile ratio of the cuff biasing elastic members 30 may be set to 1.8 and a tensile ratio of the second sheet 26 may be set to 1.4. Preferably, a differential tensile ratio between the cuff biasing elastic members 30 and the second sheet 26 may be set to about 30% or lower.

Figure 4:
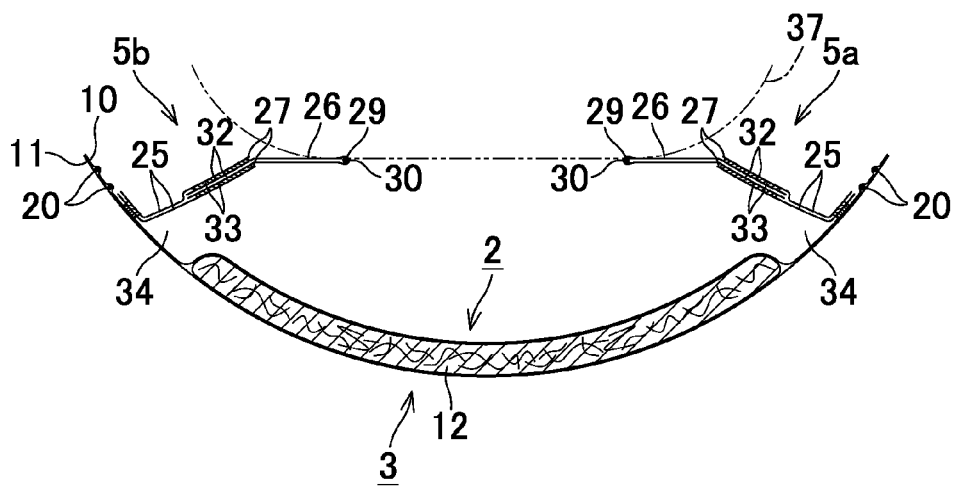
FIG. 4 is a view similar to FIG. 2, showing the diaper as put on the wearer's body.

FIG. 4 shows the diaper 1 as put on the wearer's body wherein the first and second barrier cuffs 5a, 5b are kept in contact with the wearer's skin under the wearer's body weight. According to this embodiment, the outside portion 32 of the second sheet 26 is overlapped and joined to the notch 27 of the first sheet 25 and this first sheet 25 has a stiffness higher than that of the second sheet 26. The joint zone 33 at which these components are overlapped and joined to each other has a stiffness higher than the remaining portion. The second sheet 26 is bent along the joint zone 33 as the wearer's body weight is exerted on the second sheet 26. The second sheet 26 bent in this manner comes in contact with the wearer's skin substantially in parallel thereto so that the contact area can be maximized and thereby irritation of the wearer's skin 37 due to a localized intense contact with the wearer's skin 37.

According to this first embodiment, a dimension A of the diaper 1 in the crotch region 8 as measured in the transverse direction X was set to about 130 mm and dimensions B1 and B2 of the first and second barrier cuffs 5a, 5b as measured from the respective outermost edges 21 to the respective innermost edges 24 in the transverse direction X were set to about 45 mm. Taking account of a dimensional reduction under the effect of the leg elastic members 20, the measurement of the dimension A was carried out inside the leg elastic members 20 from the outermost edge 21 of the first lateral half 5a to the outermost edge 21 of the second barrier cuff 5b.

A dimension C as measured from the innermost edge 24 of the first barrier cuff 5a to the innermost edge 24 of the second barrier cuff 5b in the transverse direction X was set to about 40 mm. While these dimensions depend on a size of the diaper 1 as a whole and may be appropriately varied, a sum of the respective dimensions B1 and B2 of the first and second barrier cuffs 5a, 5b is preferably in a range of about 40 to about 95% of the dimension A and more preferably about 50% or more. By setting the dimensions B1, B2 relatively large in this manner, the dimension C between the first and second barrier cuffs 5a, 5b can be correspondingly reduced and thereby the wearer's skin can be protected from direct contact with the liquid-absorbent structure. By setting the dimension between the first and second barrier cuffs 5a, 5b in the transverse direction X relatively large, a distance by which these barrier cuffs 5a, 5b are spaced from the topsheet 10 can be correspondingly increased and thereby the pockets 34 defined between these first and second barrier cuffs 5a, 5b and the first topsheet 10 can be enlarged.

A dimension E as measured from the front end 22 to the rear end 23 of the first sheet 25 may be set equal to a dimension as measured from the front end 17 to the rear end 18 of the liquid-absorbent chassis 4 to ensure that the first and second barrier cuffs 5a, 5b can be formed so as to extend over the entire area of the liquid-absorbent chassis 4 in the longitudinal direction Y. A dimension D in the longitudinal direction Y over which the second sheet 26 partially exposed outward from the notch 27 is about 255 mm and the dimension E of the first sheet 25 is about 395 mm. The dimension D is preferably 50% or more of the dimension E. The dimension D may be set relatively large in comparison to the dimension E to ensure that the inner most edge 24 of the second sheet 26 extends over a relatively long range in the longitudinal direction Y. In this way, formation of gathers can be effectively restrained and irritation of the wearer' skin can be minimized.

It will be appreciated that the second sheet 26 has a required elasticity in itself and relies on no other separately provided means such as an elastic member.

Figure 5C:
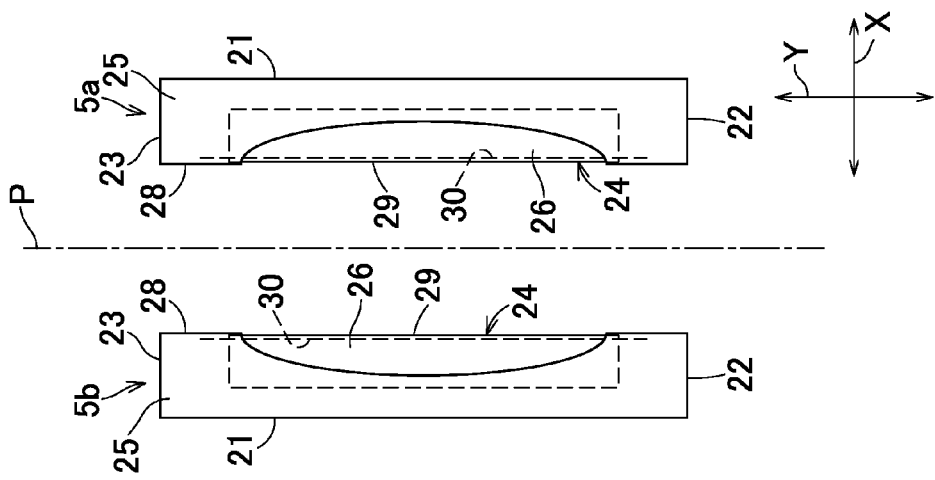
FIGS. 5A-5C are schematic diagrams illustrating a method for making the barrier cuffs according to the first embodiment.

A method for making the first and second barrier cuffs 5a, 5b will be described with reference to FIG. 5. FIG. 5A illustrates a first step. In this first step, the first sheet 25 is formed with a pair of openings 35 which are symmetric about the longitudinal center line P-P and extend in the longitudinal direction Y. The first sheet 25 is coated along these openings 35 with hot melt adhesive 36.

Figure 5B:
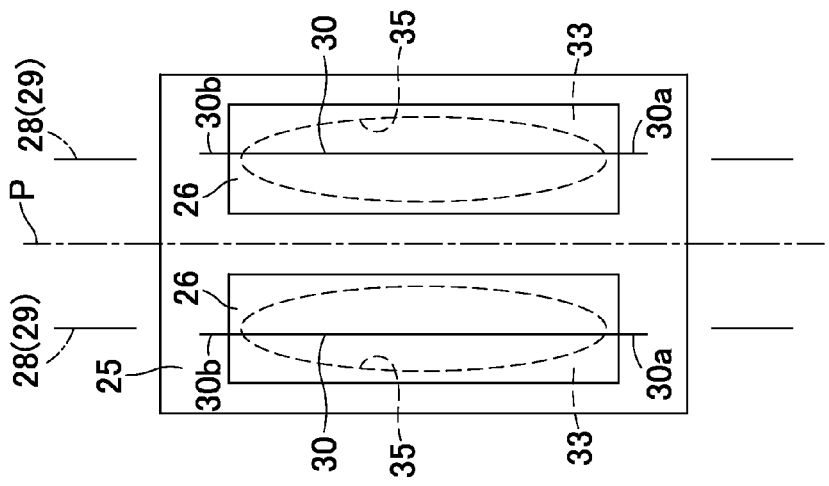
Figure 5A:
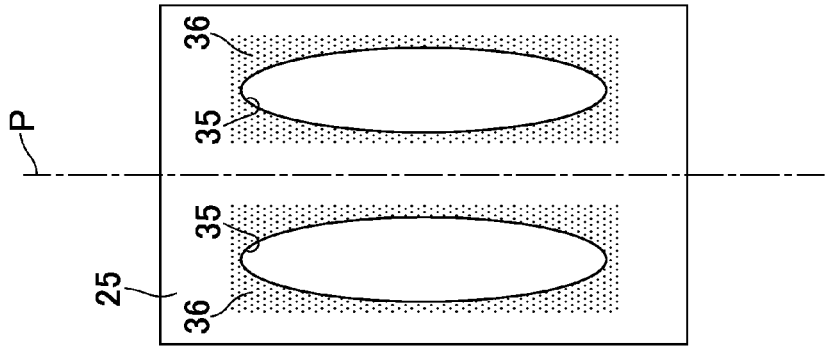

FIG. 5B illustrates second and third steps. In the second step, the second sheet 26 is joined to the first sheet 25 so as to cover the openings 35 having been formed in the first step. While the second sheet 26 is dimensioned sufficiently large to cover the openings 35, a dimension of the second sheet 26 as measured in the longitudinal direction Y is set to be shorter than the corresponding dimension of the first sheet 25. The second sheet 26 is intermittently joined under tension to the first sheet 25 by means of the hot melt adhesive 36 having been applied in the first step and thereby the joint zone 33 is formed.

In the third step, the cuff biasing elastic members 30 are laid along the fold lines 28, 29 each bisecting a dimension of the opening 35 in the transverse direction X and extending in the longitudinal direction Y, followed by fixing the front and rear ends 30a, 30b of the cuff biasing elastic members 30 to the first sheet 25 by means of adhesive (not shown).

FIG. 5C illustrates a fourth step. In this fourth step, the first sheet 25 to which the second sheet 26 has been joined is cut along the longitudinal center line P-P. The first sheet 25 having been cut in this manner is folded back together with the second sheet 26 along the fold lines 28, 29 so that the second sheet 26 including the joint zone 33 lies inside. In this way, the second sheet 26 is exposed in the openings 35 of the first sheet 25. The first sheet 25 and the second sheet 26 may be folded along the cuff biasing elastic member 30 to obtain an edge defined by the cuff biasing elastic member 30.

In the manner as has been described above, the first and second barrier cuffs 5a, 5b are made.

In the first and second barrier cuffs 5a, 5b having been made through the steps as above described, the fold lines 28, 29 define the innermost edges 24 and the side edges of the first sheet 25 opposed to and spaced from the innermost edges 24 define the outermost edges 21. The first and second barrier cuffs 5a, 5b have the respective outermost edges 21 opposed to and attached to the side edges 13 of the liquid-absorbent chassis 4 and the first sheet 25 lying along the outermost edges 21 and the front and rear ends 22, 23 is joined to the topsheet 10.

According to this method for making, the first sheet 25 is formed with a pair of the notches 27 from the openings 35 and the first sheet 25 is bisected along the longitudinal center line P-P to make the first and second barrier cuffs at once. Consequentially, the number of steps for making the barrier cuff can be correspondingly reduced in comparison to the case in which the first and second barrier cuffs 5a, 5b are separately made. An inelastic, substantially non-extensible material used as the base material for the first and second barrier cuffs 5a, 5b is relatively easy to handle in comparison to the case in which an elasticized sheet is used and a production cost can be correspondingly reduced.

The size of the second sheet 26 is not specified so far as it is sufficiently large to cover the openings 35. Even if a dimensional error is observed in the course of pulling out elasticized fibrous nonwoven fabric from a feed roll and successively cutting this, it is not apprehended that the functionality of the barrier cuff might be affected by such dimensional error and, by contrast, the barrier cuff can be easily made using the conventional equipment.

Second Embodiment

Figure 6:
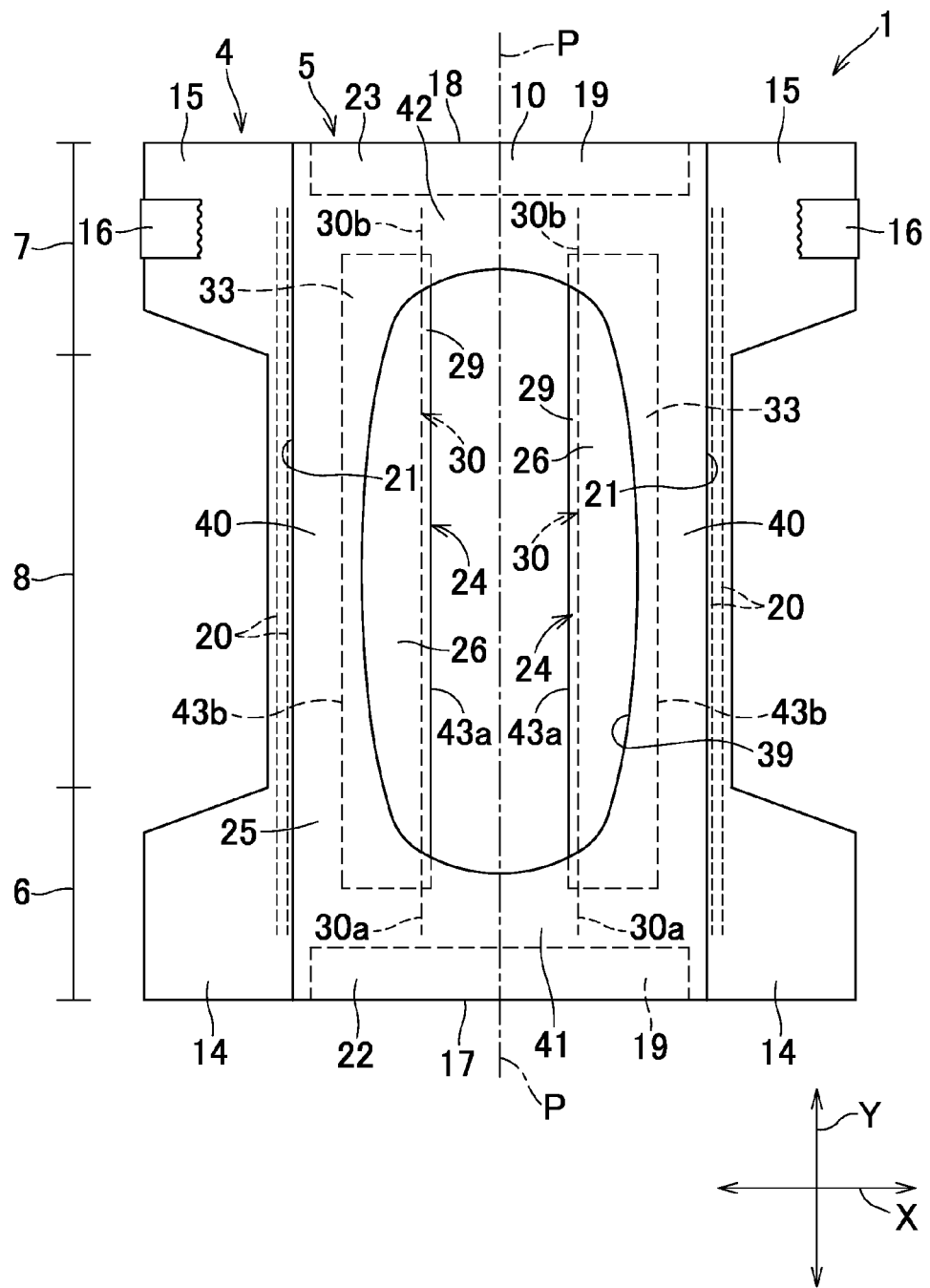
FIG. 6 is a plan view showing the diaper according to a second embodiment.

FIG. 6 is a view similar to FIG. 1, showing a second embodiment of the present invention. According to this embodiment, the barrier cuff 5 is distinguished from the first embodiment in its configuration. The other features are similar to those in the first embodiment and description thereof will be omitted here. As shown, the barrier cuff 5 comprises a single first sheet 25 forming the fixed edges and a pair of second sheets 26 forming the free edges. The first sheet 25 has a rectangular shape wherein a dimension as measured from the front end 22 to the rear end 23 is substantially the same as a dimension as measured from the front end 17 to the rear end 18 of the liquid-absorbent chassis and a dimension as measured from one of the outermost edges 21 to the other outermost edge 21 is substantially the same as a dimension as measured from one of the leg elastic members 20 to the other leg elastic member 20.

The first sheet 25 is formed in its central zone with an opening 39 extending in the longitudinal direction Y so as to cross the longitudinal center line P-P, leaving a pair of barrier cuffs 40 in the transverse direction X of the opening 39 and front and rear portions 41, 42 in the longitudinal direction Y. Two pieces of the second sheet 26 which are folded in two and extend in the longitudinal direction Y underlie the barrier cuffs 40 and partially exposed in the opening 30. Each of the second sheets 26 is folded back along the fold line 29 and this fold line 29 exposed in the opening 39. The fold line 29 contains therein the cuff biasing elastic member 30 extending along this fold line 29 and attached under tension to the second sheet 26. The second sheet 26 is joined to the first sheet 25 by means of the joint zone 33 while the front and rear ends 30a, 30b of the cuff biasing elastic member 30 is fixed as the second sheet 26 is joined to the first sheet 25 by adhesive or welding technique.

One of the barrier cuffs 40 of the first sheet 25 cooperates with the second sheet 26 joined to the barrier cuffs 40 to define the first barrier cuff 5a while the other barrier cuff 40 cooperates with the second sheet 26 joined to this to define the second barrier cuff 5b. The first and second barrier cuffs 5a, 5b are contiguous to each other by the intermediary of the front and rear portions 41, 42.

With the diaper 1 according to this second embodiment put on the wearer's body, the crotch region 8 is curved concavely toward the outside of the diaper 1 and the second sheets 26 in the first and second barrier cuffs 5a, 5b as well as the cuff biasing elastic member 30 contract. Thereupon, the second sheets 26 defining the respective free edges are spaced from the topsheet 10 to form the pockets. The first and second barrier cuffs 5a, 5b are contiguous to each other via the front and rear portions 41, 42 and these front and rear portions 41, 42 also are spaced from the topsheet 10 to participate formation of the pockets. In this way, it is possible to form the pockets in a vast area of the crotch region and thereby to prevent further reliably bodily fluids from leaking out.

FIG. 7 illustrates a method for making the barrier cuff 5 according to the second embodiment. In a first step as illustrated in FIG. 7A, the first sheet 25 is formed in its central zone with an opening 39 extending in the longitudinal direction Y so as to cross the longitudinal center line P-P. A pair of barrier cuffs 40 left outside the opening 39 is coated around the opening 39 with hot melt adhesive 36.

In a second step as illustrated by FIG. 7B, a pair of the second sheets each extending in the longitudinal direction Y are joined to the barrier cuffs 40 of the first sheet 25. The second sheet 26 is formed substantially in a middle as viewed in the transverse direction X thereof with a fold line 29 extending in the longitudinal direction Y and one of the cuff biasing elastic members 30 is provided along this fold line 29. Each of the second sheets 26 is folded back along the fold line 29 to contain therein the associated cuff biasing elastic member 30. The second sheet 26 having been folded back in this manner is joined to the first sheet 25 in the joint zone 33 by the hot melt adhesive 36. The front and rear ends 30a, 30b of the cuff biasing elastic members 30 are joined to the first sheet 25 by adhesive or welding technique.

The barrier cuff 5 made in this manner has its surface on the anterior of the draft sheet opposed to and joined to the topsheet 10 by adhesive or welding technique.

According to this method for making the barrier cuff, it is unnecessary to cut the first and second sheets after these two sheets are joined to each other and the number of steps can be correspondingly reduced. While the first sheet 25 is used as a single layer, it is possible to use it in the form of double layers.

The invention claimed is:

1. An absorbent wearing article comprising:
a liquid-absorbent chassis having a longitudinal direction, a transverse direction, an inner side facing the article wearer's skin, an outer side facing the article wearer's garment, a front waist region, a rear waist region, a crotch region between these front and rear waist regions;
a liquid-absorbent structure provided so as to occupy at least said crotch region; and
a barrier cuff provided on said inner side facing the article wearer's skin of said liquid-absorbent chassis so as to extend in said longitudinal direction,
said barrier cuff comprises:
a pair of first and second side cuffs opposed to and spaced from each other symmetrically about a longitudinal center line bisecting a dimension of the article in said transverse direction so as to extend in said longitudinal direction;
each of said first and second side cuffs comprises an outermost edge extending in said longitudinal direction, an innermost edge lying aside from said outermost edge toward said longitudinal center line, a fixed edge formed by an inelastic first sheet fixed to the liquid-absorbent chassis at least in the vicinity of said outermost edge and a free edge being spaceable from said liquid-absorbent chassis at least partially along said innermost edge and formed by an elastically extensible second sheet; and
said second sheet is attached to said first sheet under tension in said longitudinal direction so that, with said absorbent wearing article put on the article wearer's body, formation of gathers along said innermost edges in said longitudinal direction is prevented,
wherein said barrier cuff includes front and rear ends opposed to and spaced apart from each other in said longitudinal direction and said barrier cuff has said outermost edges as well as said front and rear ends formed by said first sheet, said innermost edges formed with notches and said second sheet joined to said first sheet so as to fill said notches.

2. The absorbent wearing article according to claim 1, wherein, with said absorbent wearing article flatly developed, a sum of respective dimensions of said pair of first and second barrier cuffs as measured in the transverse direction is in a range of about 40% to about 95% of a dimension of said absorbent wearing article in said crotch region as measured in said transverse direction.

3. The absorbent wearing article according to claim 1, wherein:
Said first and second side cuffs include cuff biasing elastic members attached under tension to said barrier cuff so as to extend in said longitudinal direction from said front end to said rear end;
said front and rear ends are formed by said first sheet; and
front and rear ends of said cuff biasing elastic members are fixed to said front and rear ends formed by said first sheet.

4. The absorbent wearing article according to claim 1, wherein said second sheet is partially sandwiched and affixed between two layers of said first sheet having been folded back.

5. The absorbent wearing article according to claim 1, wherein a stiffness of said first sheet is set to be higher than a stiffness of said second sheet.

6. A method for making an absorbent wearing article comprising a liquid-absorbent chassis having a longitudinal direction, a transverse direction, an inner side facing the wearer's skin, an outer side facing the article wearer's garment, a front waist region, a rear waist region, a crotch region between these front and rear waist regions and a liquid-absorbent structure provided so as to occupy at least said crotch region, and a barrier cuff provided on said inner side facing the wearer's skin of said liquid-absorbent chassis so as to extend in said longitudinal direction, said method comprising the steps of:

making said liquid-absorbent chassis;

making said barrier cuff;

attaching said barrier cuff to said liquid-absorbent chassis;

said step of making the barrier cuff comprising the steps of:

forming an inelastic first sheet with a pair of openings spaced from each other in said transverse direction symmetrically about a longitudinal center line bisecting a dimension of said first sheet and extending in said longitudinal direction;

joining an elastically extensible second sheet under tension to said first sheet so as to cover said openings;

attaching elastic members under tension to said first sheet at front and rear ends to said elastic members along a fold line bisecting a dimension of said openings as measured in said transverse direction; and cutting said first sheet to which said second sheet has been joined along said longitudinal center line and then folding back said first and second sheets along said fold line.

\* \* \* \* \*